(12) United States Patent
Roth

(10) Patent No.: US 11,813,021 B2
(45) Date of Patent: Nov. 14, 2023

(54) COLOR VISION VARIABILITY TEST SYSTEM

(71) Applicant: natific AG, Aesch (CH)

(72) Inventor: Andreas Roth, Allschwil (CH)

(73) Assignee: NATIFIC AG, Aesch (CH)

( * ) Notice: Subject to any disclaimer, the term of this patent is extended or adjusted under 35 U.S.C. 154(b) by 104 days.

(21) Appl. No.: 17/346,588

(22) Filed: Jun. 14, 2021

(65) Prior Publication Data

US 2021/0386284 A1 Dec. 16, 2021

(30) Foreign Application Priority Data

Jun. 16, 2020 (CH) .................................. 00714/20

(51) Int. Cl.
*A61B 3/06* (2006.01)

(52) U.S. Cl.
CPC .................................. *A61B 3/066* (2013.01)

(58) Field of Classification Search
CPC ....................................................... A61B 3/066
(Continued)

(56) References Cited

U.S. PATENT DOCUMENTS

| 2,937,567 A * | 5/1960 | LeGrand | ................ | A61B 3/066 351/242 |
| 4,848,898 A | 7/1989 | Massof | | |

(Continued)

FOREIGN PATENT DOCUMENTS

| EP | 1721569 A | 11/2006 |
| JP | 2019017853 A | 2/2019 |
| KR | 101485942 B1 | 1/2015 |

OTHER PUBLICATIONS

Rich, D.C. and Jalijali, J. (1995), Effects of observer metamerism in the determination of human color-matching functions. Color Res. Appl., 20: 29-35. https://doi.org/10.1002/col.5080200106 (Year: 1995).*

(Continued)

*Primary Examiner* — Zachary W Wilkes
(74) *Attorney, Agent, or Firm* — MEDLER FERRO WOODHOUSE & MILLS PLLC

(57) ABSTRACT

The present invention relates to a test system for assessing color vision variability of test persons (7). The test system comprises at least two test carriers (1), wherein each of the at least two test carriers (1) is provided with a two-dimensional pattern (4) including a background (2) and a plurality of samples (3). The plurality of samples (3) and the background (2) of each one of the at least two test carriers (1) are made of at least two different dyestuff combinations representing metameric colors. The samples (3) and/or the background (2) show color scaling in at least two directions such that each one of the at least two test carriers (1) is configured to provide that a test person (7) can select a spot ($PIS_C$) from the two-dimensional pattern (4) where the metameric colors of the samples (3) and the background (2) match best. The system further comprises a test illuminant unit (5) configured to provide light for the color vision variability assessment, the light having a specific spectral power distribution. The system further comprises a processing unit (6) configured to predict a color matching function and/or to determine a congenital and/or acquired color vision deficiency of the test person (7) by calculating a variation of the spot ($PIS_C$) selected by the test person (7) as compared to a spot (PISS) computed by the processing unit (6) based on data of a predefined standard observer considering the specific spectral power distribution of the light of the test illuminant unit (5).

16 Claims, 15 Drawing Sheets

(58) Field of Classification Search
USPC .......................................................... 351/242
See application file for complete search history.

(56) References Cited

U.S. PATENT DOCUMENTS

| | | | |
|---|---|---|---|
| 5,485,230 | A | 1/1996 | Zimmerman |
| 9,826,898 | B1* | 11/2017 | Jin .......................... A61B 3/066 |
| 10,912,457 | B2* | 2/2021 | Schmeder ............... A61B 3/066 |
| 11,096,571 | B2* | 8/2021 | Diaconu ................ A61B 3/066 |
| 2005/0195363 | A1 | 9/2005 | Sato |
| 2010/0188639 | A1* | 7/2010 | Carda .................... A61B 3/066 |
| | | | 351/242 |
| 2016/0206192 | A1 | 7/2016 | Sakakima |
| 2017/0205977 | A1* | 7/2017 | Fertik ................... G06F 3/0483 |
| 2017/0209041 | A1 | 7/2017 | Ixhikawa et al. |
| 2019/0133439 | A1* | 5/2019 | Ichikawa ............... A61B 3/066 |
| 2020/0029804 | A1* | 1/2020 | Diaconu ................ A61B 3/066 |

OTHER PUBLICATIONS

Alfvin, R.L. and Fairchild, M.D. (1997), Observer variability in metameric color matches using color reproduction media. Color Res. Appl., 22: 174-188. https://doi.org/10.1002/(SICI)1520-6378(199706)22:3<174::AID-COL6>3.0.CO;2-O (Year: 1997).*

Search Report dated Jan. 6, 2022 in corresponding Great Britain Patent Appl. No. 2108577.4.

International Search Report dated Nov. 17, 2020, in Swiss Application No. CH 00714/20.

Hunt et al., "A Colour-Appearance Transform for the CIE 1931 Standard Colorimetric Observer," Color Research & Application, (10)3, pp. 165-179, Sep. 1, 1985.

\* cited by examiner

COLOR VISION VARIABILITY TEST SYSTEM

TECHNICAL FIELD

The present invention relates to a test system for assessing color vision variability of test persons. Generally, such test systems serve for identifying various kinds of color vision deficiencies of human observers and for predicting the individual color matching functions (CMFs) of color-normal observers.

BACKGROUND ART

The lenses of human beings consist of a gel-like, somewhat translucent fluid through which the perceived colors and light of reflecting objects are being transmitted. By passing through the lens, the visual image will be condensed and passed on to the retina, where it is perceived and transmitted into the optic nerves for further transport to the human brain.

Normal color vision is trichromatic. Any color stimulus is specified by three quantities, corresponding to the quantum catch in the three families of cones in the retina. Thus, the human visual system reduces the physical information in the light spectrum to three signals and does not perceive many variations within that spectrum. This explains metamerism, a property of color stimuli that are spectrally different and still have the same tristimulus values.

Congenital color vision deficiencies among human observers are usually caused by a fault in the development of one or more sets of retinal cones that perceive color in light and transmit that information to the optic nerve. There are several tests applied in the industry to check congenital color deficiencies. Congenital color vision deficiencies are found in ~8% of males and ~0.5% of females. The different classifications of congenital color vision deficiencies are related with the number of malfunctioning sets of retinal cones (monochromasy, dichromasy and anomalous trichromacy), which of the set of cones shows a malfunction (protanomaly, deuteranomaly, tritanomaly), respectively which set of cones is absent (protanopia, deuteranopia, tritanopia).

The Ishihara Color Test, named after its designer, Dr. Shinobu Ishihara and based on pseudo-isochromatic plates is an example of a color perception test for red-green color deficiencies (protanopia and deuteranopia).

The Farnsworth-Munsell 100 Hue Color Vision Test is another test of the human visual system used to test for congenital color vision deficiencies. The system was developed by Dean Farnsworth in the 1940s and it tests the ability to isolate and arrange minute differences in various color targets with constant value and chroma that cover all the visual hues described by the Munsell color system.

Color vision deficiencies of human observers can also be acquired. Reasons for an acquired color vision deficiency may be ocular pathology, intracranial injury, and excessive use of therapeutic drugs or preretinal filters such as colored glasses or lenses, selective absorption by the lens, by the macular pigment or caused by the photopigment spectral absorbance and the length of the photoreceptors.

It is necessary to mention the special features of preretinal filters where the lens pigment optical density, generally caused by the yellowing of the lens, increases with the age of the observer and where the impact of the macular pigment optical density is varying with the field size.

An example of a color perception test to evaluate acquired color vision deficiencies includes the Glenn Color Rule, the Davidson and Hemmendinger Color Rule (D&H Color Rule) and the Macbeth Matchpoint. These tests have a series of metameric color samples arranged in pairs where the observer's task is to find a pair of samples that appear the same according to their perception. The selected pair for a single illumination is used to evaluate observer metamerism.

Color vision deficiencies can also be detected by a kind of apparatus that emits a mixture of monochromatic light sources. An example of such an apparatus is the anomaloscope which provides the possibility to test the severity of color blindness and distinguish between dichromats and anomalous trichromats. These apparatuses are widely used but show limitations in detecting acquired color vision deficiencies. They often are expensive and in general not used to test observers that are responsible for color assessments in the global industry. The observation of pigmented surfaces such as those of the D&H Color Rule or colored fabrics such as used in other color vision tests is closer to everyday experience than is the observation of mixtures of monochromatic lights such as used in anomaloscope.

Visual methods of color matching can be haphazard and are notoriously unreliable for a number of reasons. These include the absence of standard illuminants and viewing conditions and the subjective and psychological nature of the human observer. The variability among color-normal observers poses a challenge to visual color assessment. For digital color management, color reproduction relies on colorimetric data for a single "standard observer", representing an average colorimetric observer with normal color vision. Only colorimetric observers such as colorists who are sufficiently close to such a standard observer shall apply for pass/fail decisions for colors.

The CIE 1931 standard colorimetric observer and the CIE 1964 standard colorimetric observer, also known as 2° and 10° standard observers have been developed by the Commission Internationale de l'Eclairage (CIE) also known as International Commission on Illumination, an organization devoted to international cooperation and exchange of information among its member countries on matters relating to the science and art of lighting/illumination. These standard observers, representing an average human observer, have satisfied industries for many decades.

However, the advent of narrowband fluorescent lamps and LEDs is changing this situation. The use of a standard observer is based on the assumption that a single observer or a single set of color matching functions (CMFs) can reasonably represent a whole population of people with normal color vision. Narrowband stimuli, however, increase the individual differences in CMFs. The 1964 CIE 10° and the 1931 CIE 2° standard observer are still widely used in the industry for digital color management.

It is important to recognize that the best possible representation of the population of color-normal observers is critical. The CIE-2° and the CIE-10° standard observer—at best—represent a close average of all human observers but do not consider the variations such as related to age, by region or by gender. The above standard observers were not developed under practical viewing conditions (physical samples/specific viewing angle/specific light sources as found in common light cabinets).

The variability among individual observers is widely recognized. However, still no new standard deviate observers were adopted by the industry. Standard deviate observers such as developed by CIE (Technical Report CIE 170-1:

2006 and CIE 170-2:2006) were not accepted as the model significantly under-predicted inter-observer variability.

It is therefore an object of the present invention to provide for a color vision variability test system by means of which the above-described deficiencies may be overcome.

DISCLOSURE OF THE INVENTION

According to the present invention this object is solved by a test system as defined in independent claim 1. Preferred embodiments are subject of the dependent claims.

In one aspect, the present invention is a test system for assessing color vision variability of test persons. The test system comprises at least two test carriers, wherein each of the at least two test carriers is provided with a two-dimensional pattern including a background and a plurality of samples. The plurality of samples and the background of each one of the at least two test carriers are made of at least two different dyestuff combinations representing metameric colors (showing different color constancies). The samples and/or the background show color scaling in at least two directions (generally two-dimensional color scaling) such that each one of the at least two test carriers is configured to provide that a test person can select a spot ($PIS_C$) from the two-dimensional pattern where the metameric colors of the samples and the background match best. The test system also comprises an illuminant unit configured to provide light for the color vision variability assessment, the light having a specific spectral power distribution (SPD). Further, the test system comprises a processing unit configured to predict a color matching function and/or to determine a congenital and/or acquired color vision deficiency of the test person by calculating a variation of the spot ($PIS_C$) selected by the test person as compared to a reference spot (PISS) computed by the processing unit based on data of a predefined standard observer considering the specific spectral power distribution of the light of the illuminant unit.

The "processing unit" applies a generic algorithm to predict the color matching functions (CMFs) and/or determine color vision deficiencies based on a particular standard observer (e.g., CIE Standard Observer 1964-10°) and based on the particular spectral power distribution (SPD) of the test illuminant unit. In particular, the "processing unit" applies a generic algorithm which may derivate individual causes for a color vision variation such as the relative spectral optical density of the lens, the macular pigment optical density, the peak optical density of the visual pigments in the outer segments of the photoreceptors, and the variation maximum wavelength of the cone fundamentals.

The "test carriers" can be in the form of physical test plates or they may be displayed e.g., on a calibrated screen.

"Color constancy" is an example of subjective constancy and a feature of the human color perception system which ensures that the perceived color of objects remains relatively constant under varying illumination conditions. A green apple for instance looks green to us at midday, when the main illumination is white sunlight, and also at sunset, when the main illumination is red. This helps identify objects.

In colometry, "metamerism" is a perceived matching of colors with different (nonmatching) spectral power distributions. Colors that match this way are called metamers. A spectral power distribution describes the proportion of total light given off (emitted, transmitted, or reflected) by a color sample at each visible wavelength; it defines the complete information about the light coming from the sample. However, the human eye contains only three color receptors (three types of cone cells), which means that all colors are reduced to three sensory quantities, called the tristimulus values. Metamerism occurs because each type of cone responds to the cumulative energy from a broad range of wavelengths, so that different combinations of light across all wavelengths can produce an equivalent receptor response and the same tristimulus values or color sensation. In color science, the set of sensory spectral sensitivity curves is numerically represented by color matching functions.

The spot ($PIS_C$) from each two-dimensional pattern where the metameric colors of the samples and the background match best is also referred to as pseudo-isochromatic spot.

Preferably, the at least two test carriers comprise a test carrier with color scaling in smaller steps (little color deviations) and a test plate with color scaling in larger steps (bigger color deviations). The variation in the extent of color scaling serves for optimal identification of acquired or congenital color vision deficiencies. An exemplary color scaling scheme is shown and described below in connection with FIG. 1.

Preferably, the samples of at least one test carrier are configured such that their color scaling is in-line with their spatial distance. This configuration is advantageously performed in accordance with a DIN 99 color space or a similar color space with high uniformity.

Preferably, each of the two-dimensional patterns comprise a grid structure. Such structures may comprise mesh-like grid structures, dotted grid structures or checkered grid structures (i.e., where sample and background have the same form), or the like.

Preferably, the samples and/or the background show color scaling in four directions. Thereby, 0° equals yellower, 90° equals redder, 180° equals bluer and 270° equals greener. Optionally, the samples may also be in the form of strips showing color scaling in two directions.

Preferably, the at least two test carriers are in book-like form having different colors and patterns. However, the at least two test carriers may also be displayed on a calibrated screen in the form of multiple pictures having different colors and patents.

Preferably, the test carriers include patterns of different size. This may be applied together with varying viewing distance, i.e., in order to distinguish between effects of existing pre-retinal filters and to derive compatible cone fundamentals for various field sizes.

Preferably, the test system further comprises a measuring device configured to measure the spectral power distribution (SPD) of the illuminant unit. The measured results are fed into the processing unit. Advantageously, the test illuminant unit comprises a light cabinet that simulates daylight.

Preferably, the data of the predefined standard observer represents a CIE standard observer. The CIE standard observer may be a CIE-1964-10° standard observer at CIE-D65 standard daylight. Alternatively, the CIE standard observer may also be a CIE-1931-2° standard observer at CIE-D65 standard daylight.

Preferably, the test carriers include special test carriers configured to provide that no best matching spot is found by test persons with normal color vision but by test persons having a congenital or aquired color vision deficiency, i.e., such as monochromasy, dichromasy or *anomalus* trichromacy. Variations in the color vision of test persons with normal vision may not be recognized by the above-mentioned tests. The aim of the special test carriers is to adopt the colors in such a way that monochromasy, dichromasy and *anomalus* trichromacy find a pseudoisochromatic spot in at least one carrier and thus the dyschromatopsia may be identified.

Preferably, the processing unit may form a color vision variability index based on the variations of the spots selected by the test person as compared to spots computed based on the data of the predefined standard observer. The color vision variability index is formed by an (generic) algorithm that is based on the color difference between the pseudo-isochromatic spot selected by a test person wherein the color difference used for the algorithm is based on an average for multiple plates.

As one can derive from the above, the principle of the present invention is based on a test person's assessment in selecting the spot from a two-dimensional pattern (geometric shapes) where the metameric samples form the best match (pseudo-isochromatic spot). The basic procedure to obtain the color matching functions (CMFs) from a tested person is based on the variation to a standard observer e.g., such as defined by CIE.

The corresponding processing unit is used to determine/predict the color matching functions (CMFs) of the test person based on the selected pseudo-isochromatic points. A generic algorithm respectively software considers the particular spectral power distribution of the illuminant unit used during the test. The algorithm respectively software also serves to identify the specific cause of any color vision deficiency considering both, congenital and acquired color vision deficiencies. The algorithm respectively software uses the variation of the selected pseudo-isochromatic spot from the spot computed based on the data of a standard observer.

The classification of an observer by using its individual color matching functions (CMFs) allows the calculation of color differences between color standard and corresponding color sample by comparing the standard observer versus the individual observer. Colorists that show a higher difference when compared to the standard observer might not represent an average human observer and may no longer visually assess colors.

The test system according to the invention can also be used for finding a new standard observer that better represents the average of human observers or used to predict the average of a group of observers of the same age such as e.g., required by fashion brands for older generations.

Additionally, the test system according to the invention allows two individuals, one from the buyer and one from the supplier, for example, to judge how much difference there is in the way each of the two individuals sees color. When properly used, this test also supports the identification of differences in the color assessment of individual combinations of observer and illumination.

The invention includes calculating color vision variability based on the variation of either the individual pseudo-isochromatic spots selected by the test person or based on computed color results using the test person's individual color matching functions (CMFs).

The invention includes an alternative test arrangement where samples are displayed on a color calibrated screen. Samples are also displayed in two-dimensional patterns (geometric shapes) where the samples also form patterns showing a two-dimensional scaling of its colors where the scaling is individual to its direction (e.g., 0°=yellower, 90°=redder, 180°=bluer, 270°=greener). The prediction of the color matching functions (CMFs) for a tested person thereby considers that all colors presented on the screen are already calculated for the Standard Observer CIE-10° and for the spectral power distribution of the available light source (i.e. standards in physical form that match the predicted pseudoisochromatic spot on the screen; standards of this color developed with a number of different dyestuff combinations, achieving a variation in spectral curve, respectively standards with a variation in their color constancy).

The basic procedure to obtain the cone fundamentals characterizing the test person's unique color-matching functions (CMFs) is based on the CMFs of a standard observer such as defined by CIE (1931-2° and 1964-10°). The variation in the pseudo-isochromatic spot selected by the test person $PIS_C$ from the pseudo-isochromatic spot $PIS_B$ found through digital computing (CMFs of standard observer/SPD of test illuminant) is the basic information required by a corresponding generic algorithm to predict the test persons color matching functions (CMFs). The change of lens density and macular pigmentation and the shift in photopigment absorbance are the primary factors that account for the variability of the metameric color matches where the individual spectral reflectance curve shapes of the background and samples serve to predict the effect of each of these pre-retinal filters.

For applied colorimetry, the predicted color matching functions (CMFs) of individuals allow the computation of how these individuals perceive colors, how they notice differences between colored samples and how they observe metamerism. The incorporation of observer variability into computations opens a unique method of observer assessment where e.g., several pairs of metameric samples are computed by the CMFs of a standard observer and the CMFs of the test person. The variation in the computed color differences between these pairs of metameric samples is used to form a vision variability index.

The invention thus also includes forming a color vision variability index which is based on the metameric index of the sample versus the standard (in general the background of a test carrier) and the color difference between the samples in the two pseudo-isochromatic spots $PIS_B/PIS_C$: the sample that shows the same computed color than the standard under the test illumination and the sample that is selected by the test person.

A standard practice may be used for the calculation of color coordinates derived from instrumentally measured spectral data of physical samples, as for example a calculation based on the spectral power distribution of the illuminant, the spectral data of the object, and the color matching functions of a standard colorimetric observer; a calculation that is based on the standard illuminant CIE-D65 or alternatively for other standard CIE-illuminants, and illuminants as used when the test is performed; a calculation that is based on the spectral data of a physical sample such as derived by a spectrophotometer measurement; a calculation that is based on for the 1964 CIE standard observer (10° observer), alternatively also 1931 CIE standard observer (2° observer) and/or a calculation that results in coordinates in CIELAB—a color space defined by the International Commission on Illumination (CIE) in 1976.

A standard practice may be used for the calculation of the color difference of a sample versus a standard, as for example a calculation that is based on the computed color coordinates of the sample and of the standard; a mathematical equation is used to improve the Euclidean distance derived from the perceptual non-uniform CIELAB color space (e.g., CMC, CIE94, DIN99, CIEDE2000) or alternatively, the Euclidean distance in color spaces with better perceptual uniformity can be used as color difference (e.g., DIN99 or any other equivalent uniform color space).

A generic algorithm may be used with the following functions: a system for predicting a single set of color matching functions (CMFs) which can reasonably represent a single observer with normal color vision; a generic algorithm for predicting the color matching functions (CMFs) on the basis of pseudo-isochromatic spots selected by an individual observer with normal color vision; a genetic algorithm for predicting the color matching functions (CMFs) of an individual observer as a variation to the specific color matching functions (CMFs) of a standard observer; a generic algorithm to predict the characteristic of the color matching functions (CMFs) so it matches the pseudo-isochromatic spots selected by the test person when (i) colors of the metameric samples are calculated as coordinates in a color space, e.g. CIELab 1976 D65/10° or others, or when (ii) color coordinates are calculated based on the reflectance data of the background and the metameric samples, on the predicted CMFs of the individual observer and on the spectral power distribution of the illuminant used for the test, or when (iii) colors of the metameric samples in the pseudo-isochromatic spots are matching within a defined color difference tolerance.

BRIEF DESCRIPTION OF THE DRAWINGS

The system according to the present invention is described in more detail herein below by way of exemplary embodiments and with reference to the attached drawings.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
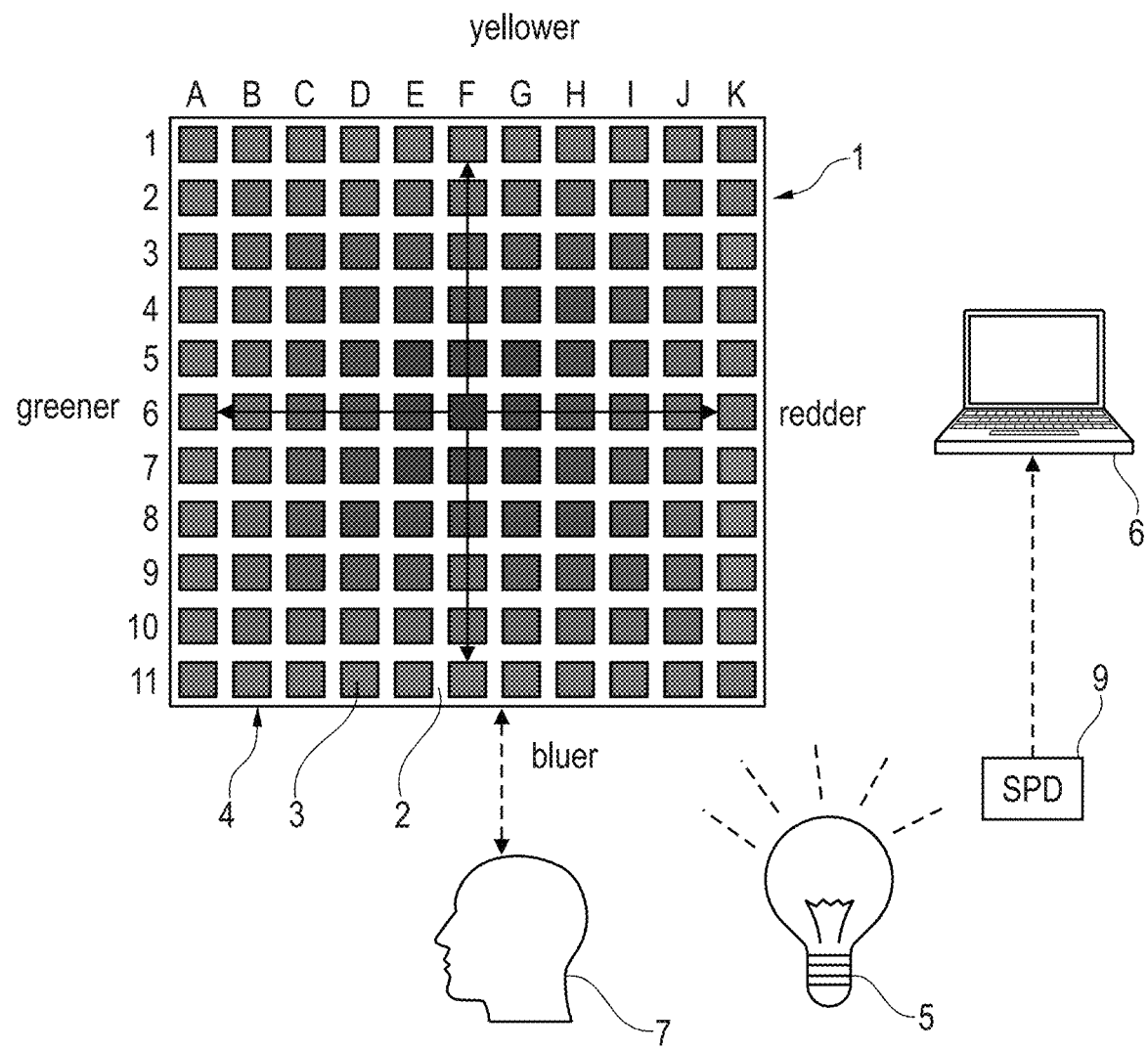
FIG. 1 shows an exemplary test carrier according to the invention with four directions of color scaling together with an exemplary environment.

FIG. 1 shows an exemplary test carrier 1 according to the invention with four directions of color scaling. The pattern 4 in each test carrier 1 is built on a background 2 color and on samples 3 colored or printed with two individual dyestuff combinations where both, the background 2 and the samples 3 show different color constancies and where the samples 3 represent metameric colors. The samples 3 building the pattern 4 show a two-dimensional scaling of its colors where the scaling is individual to its direction (e.g., 0°=yellower, 90°=redder, 180°=bluer, 270°=greener).

The four directions of color scaling "yellower, greener, redder and bluer" are changed in the physical color tests (test books) in accordance with a non-communicated scheme. This is in order to avoid that test persons learn the correct position (e.g., F6) by heart or read-off the latter for the test.

Further, in FIG. 1 the test person 7, the test illuminant unit 5, the measuring device 9 for measuring the specific spectral power distribution (SPD) of the test illuminant unit 5 and the processing unit 6 are schematically depicted. The measuring results of the measuring device 9 and the test results of the test person 7 are fed into the processing unit 6, as schematically indicated by the dashed arrows.

Figure 2:
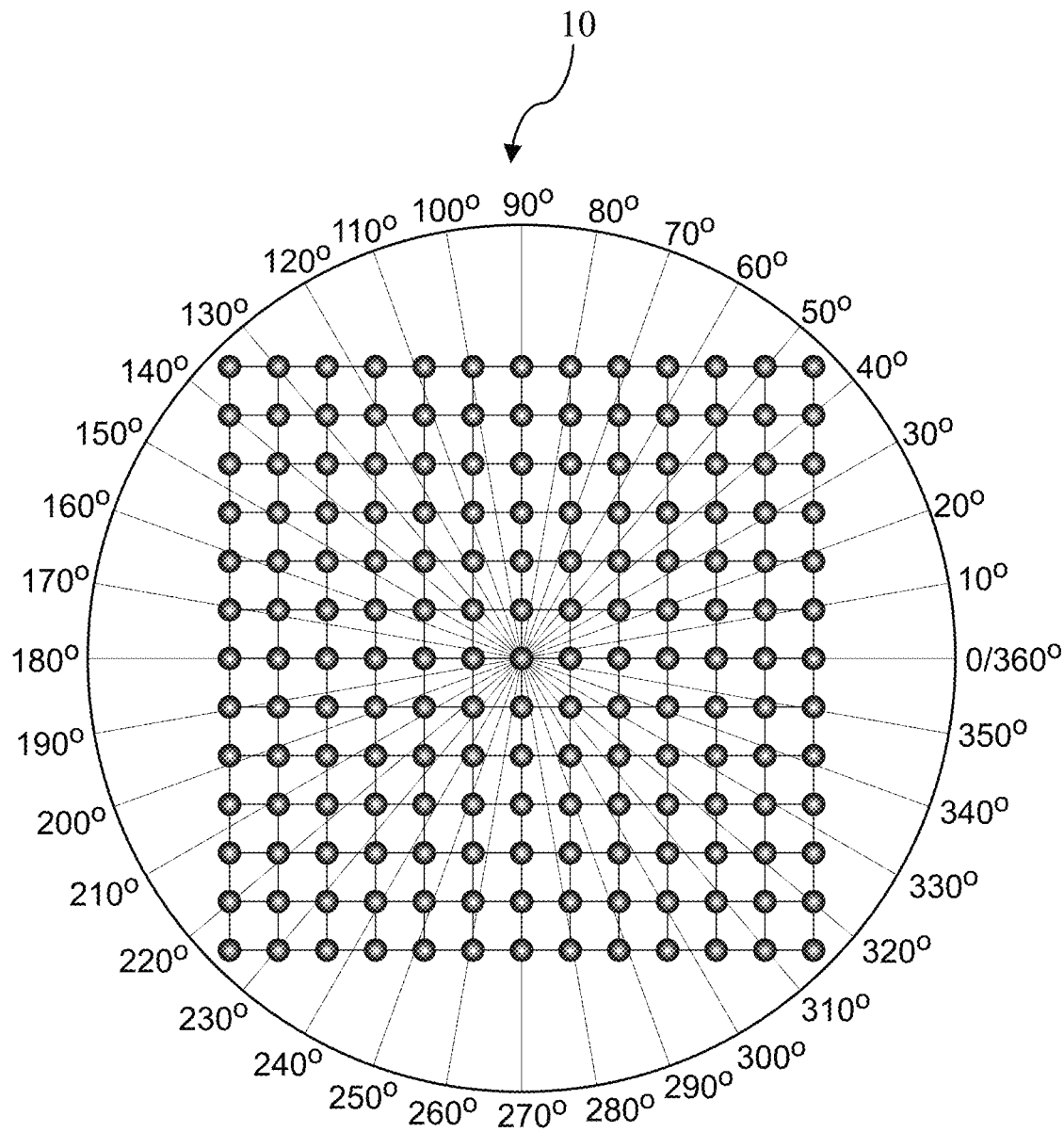
FIG. 2 shows an exemplary illustration of a DIN 99 color space.

The samples building a pattern in an individual test carrier are developed so that their color difference is in-line with their spatial distance. A proper methodology to develop the colors required for a pattern can be found in any of the available perceptual uniform color space such as for example with DIN 99 as shown in FIG. 2.

Figure 3:
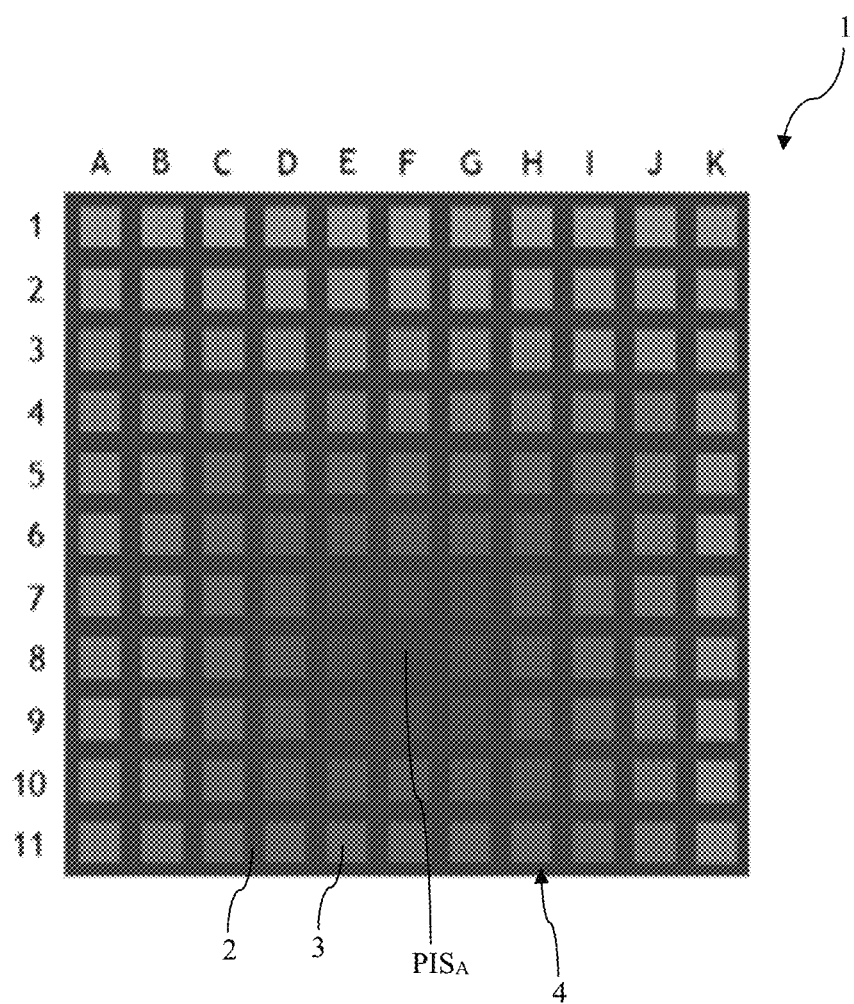
FIG. 3 shows an exemplary test carrier according to the invention with metameric samples as rectangles.

FIG. 3 illustrates an exemplary test carrier with metameric samples 3 as rectangles building a pattern 4 on a background 2 with different color constancy (i.e., different spectral reflectance curve shapes). The pseudo-isochromatic spot $PIS_A$ for the CIE-D65/10° standard observer is at position F8.

Figure 4:
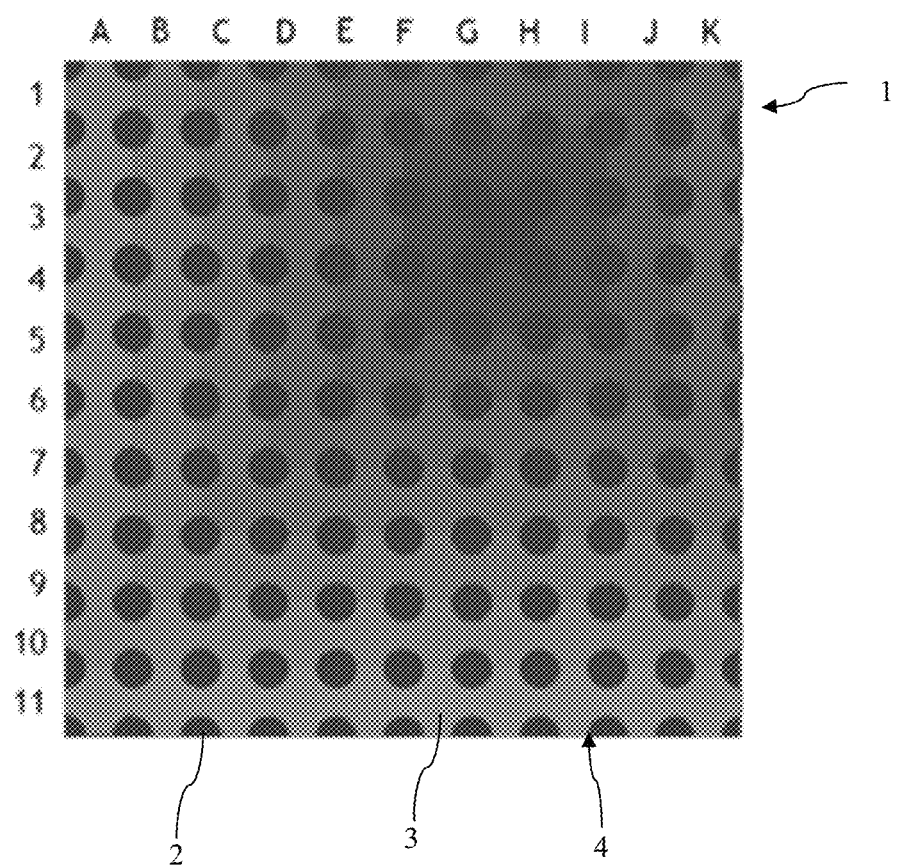
FIG. 4 shows an exemplary test carrier according to the invention where dots build the background.

FIG. 4 illustrates an exemplary test carrier where the dots build the background 2 (non-scaling color) and the surrounding area is built by metameric samples 3 with two-dimensional color scaling.

Figure 5:
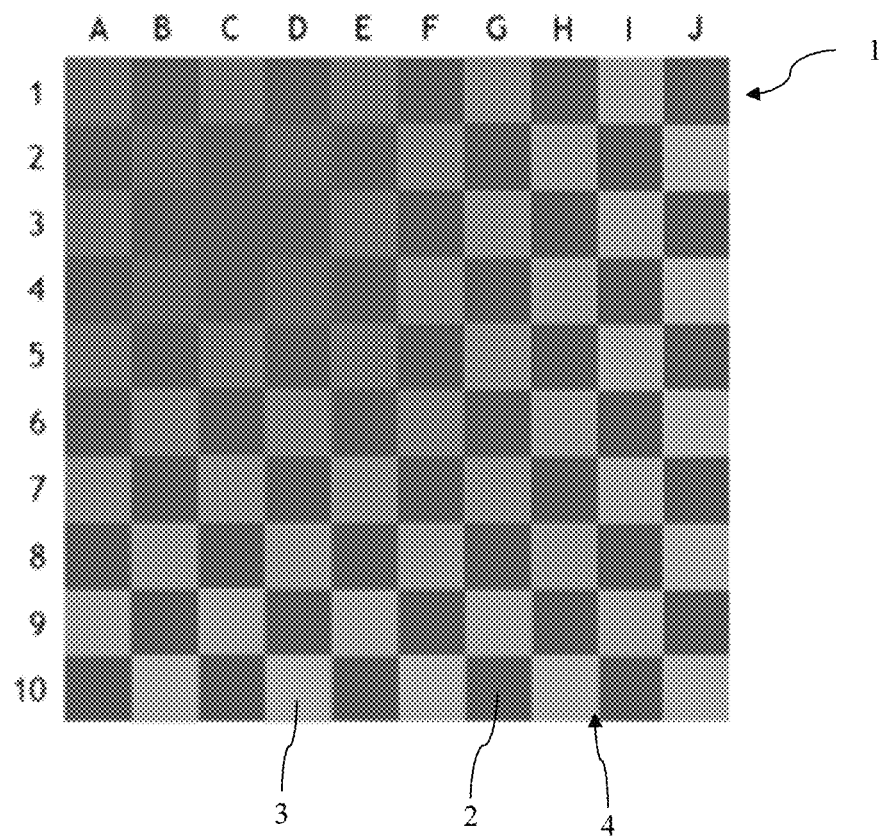
FIG. 5 shows an exemplary test carrier according to the invention where samples and background have the same form.

FIG. 5 illustrates another exemplary test carrier where samples 3 and background 2 have the same form (i.e., a checkerboard pattern) and where still only the samples 3 show two-dimensional color scaling.

Figure 6:
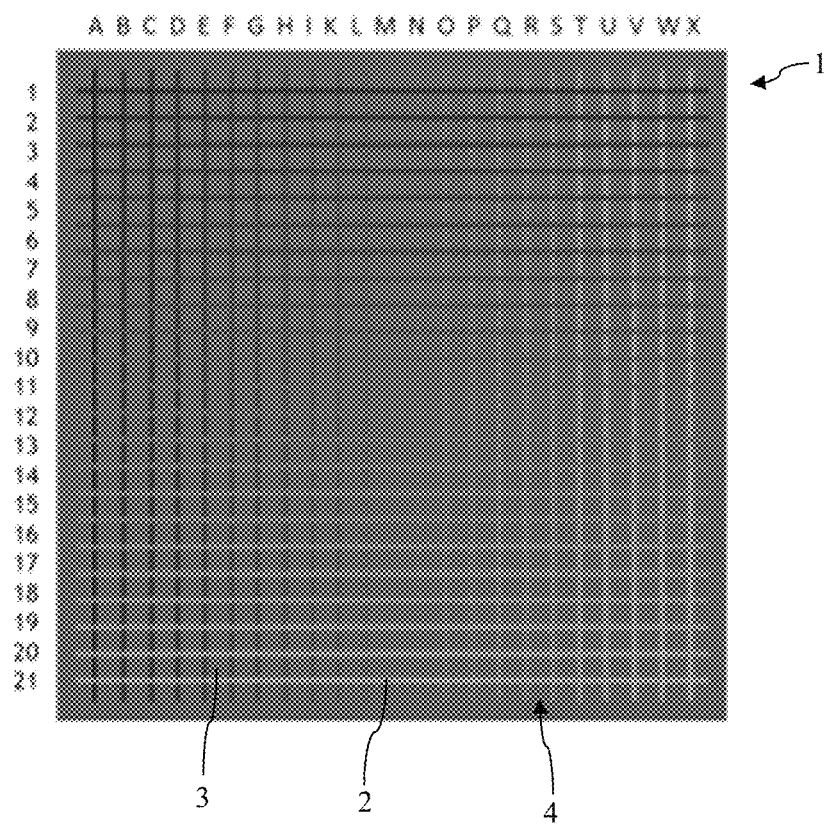
FIG. 6 shows an exemplary test carrier according to the invention where the samples are represented by strips.

FIG. 6 illustrates still another exemplary test carrier where the samples 3 are represented by strips showing color scaling in two directions. For example, the vertical strips are scaling in the direction yellow and in the direction blue; the horizontal strips are scaling in the direction green and in the direction red.

Figure 7:
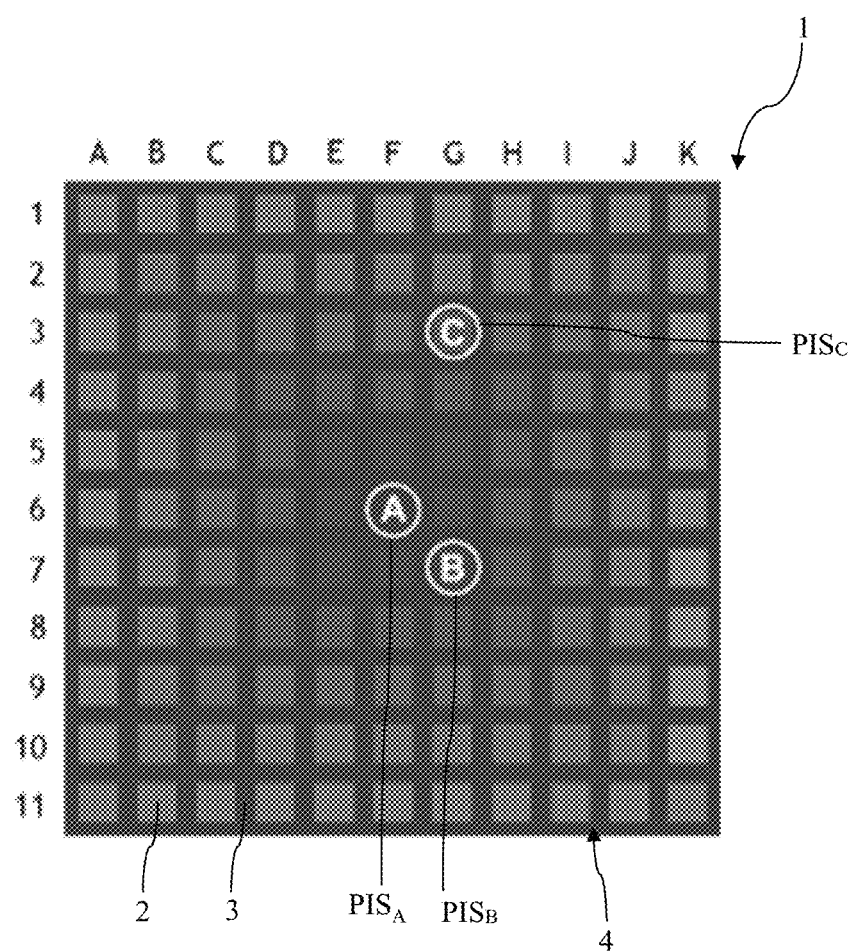
FIG. 7 shows an exemplary test carrier according to the invention with three pseudo-isochromatic spots.

FIG. 7 illustrates an exemplary test carrier (see also FIG. 1) with three individual pseudo-isochromatic spots. Spot A represents the pseudo-isochromatic spot for the standard observer CIE-10° and standard illuminant CIE-D65. Spot B represents the pseudo-isochromatic spot for the standard observer CIE-10° and the measured spectral power distribution of the test illuminant unit 5. Spot C represents the pseudo-isochromatic spot selected by a test person under the conditions of the particular test illuminant 5 (see FIG. 1)

FIGS. 8A-8D generally illustrate exemplary test carriers 1 showing the concept of the inventive color vision variability test. The example colors here are Color A (e.g., medium grey in FIGS. 8A and 8B) and color B (e.g., light brown in FIGS. 8C and 8D). The pseudo-isochromatic spot ($PIS_B$) for all carriers may be found at various positions (computed based on e.g., standard observer CIE-D65/10° for test illuminant). The background 2 and the samples 3 show variation in their color constancy (i.e., variation in their spectral reflectance curve shapes—see FIG. 10).

Figure 8A:
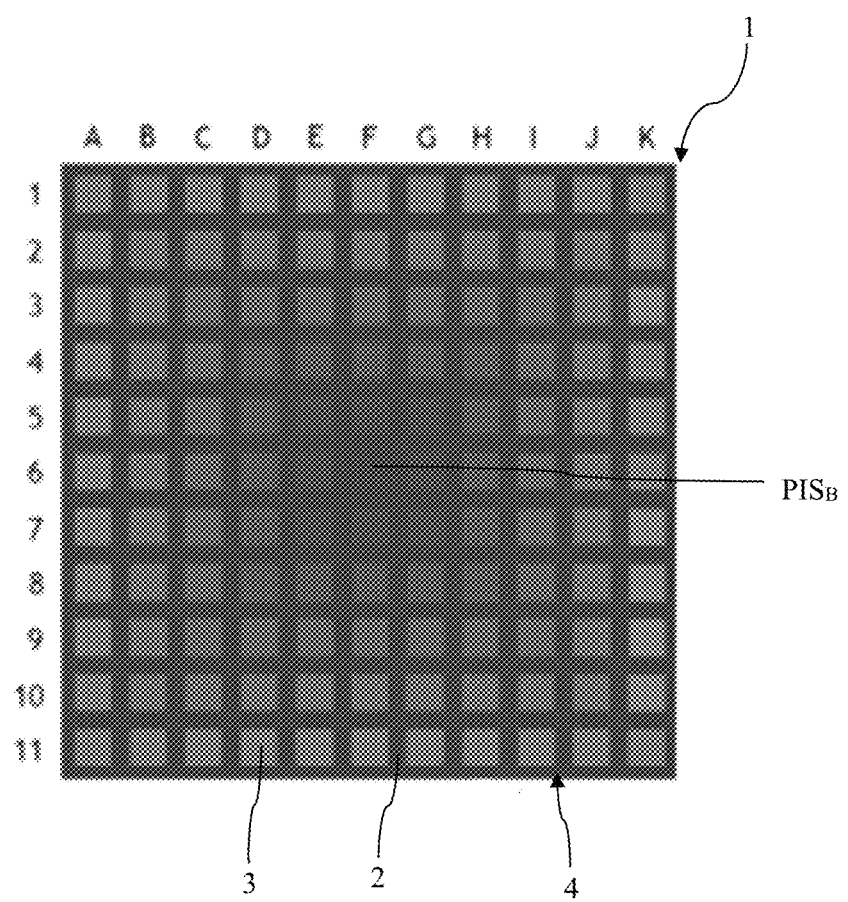
FIGS. 8A-8D show exemplary test carriers according to the invention representing the concept of the color vision variability test.

Specifically, the test carrier 1 of FIG. 8A comprises example color A (medium grey). The background 2 comprises a reflectance curve shape rf1 different from the reflectance curve shape rf2 of the samples 3 (as can be seen from FIG. 10). The pseudo-isochromatic spot $PIS_B$ is at position F6.

Figure 8B:
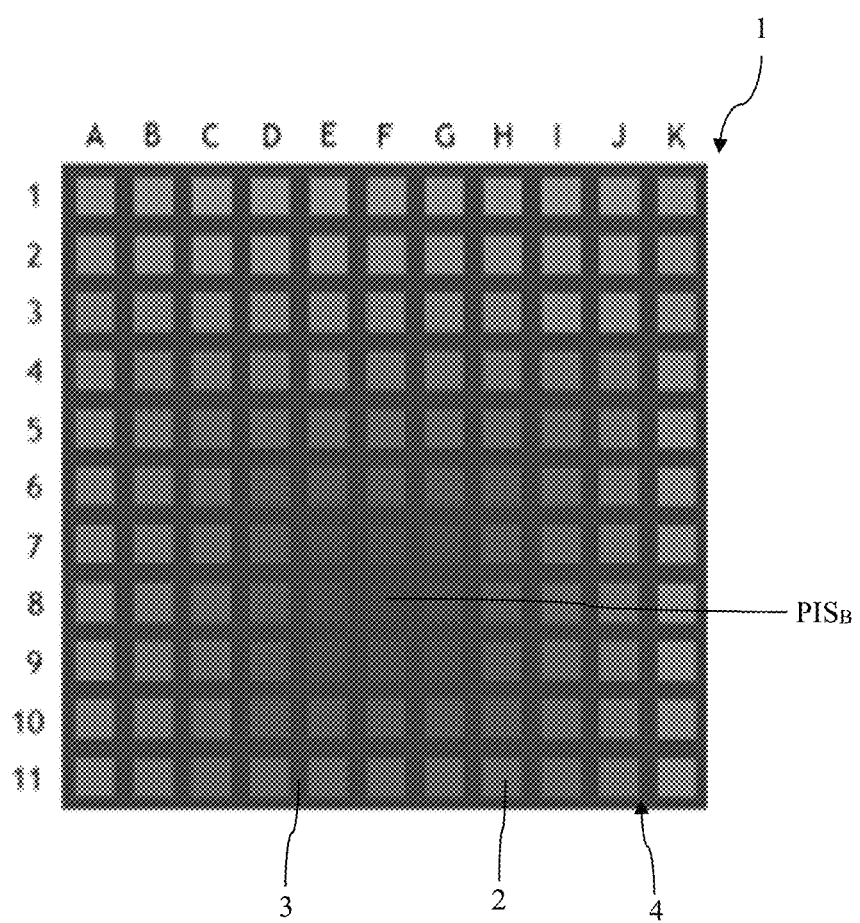

The test carrier 1 of FIG. 8B also comprises example color A (medium grey). The background 2 comprises a reflectance curve shape rf1 different from the reflectance curve shape rf2 of the samples 3 (as can be seen from FIG. 10). The pseudo-isochromatic spot $PIS_B$ is at position F8.

Figure 8C:
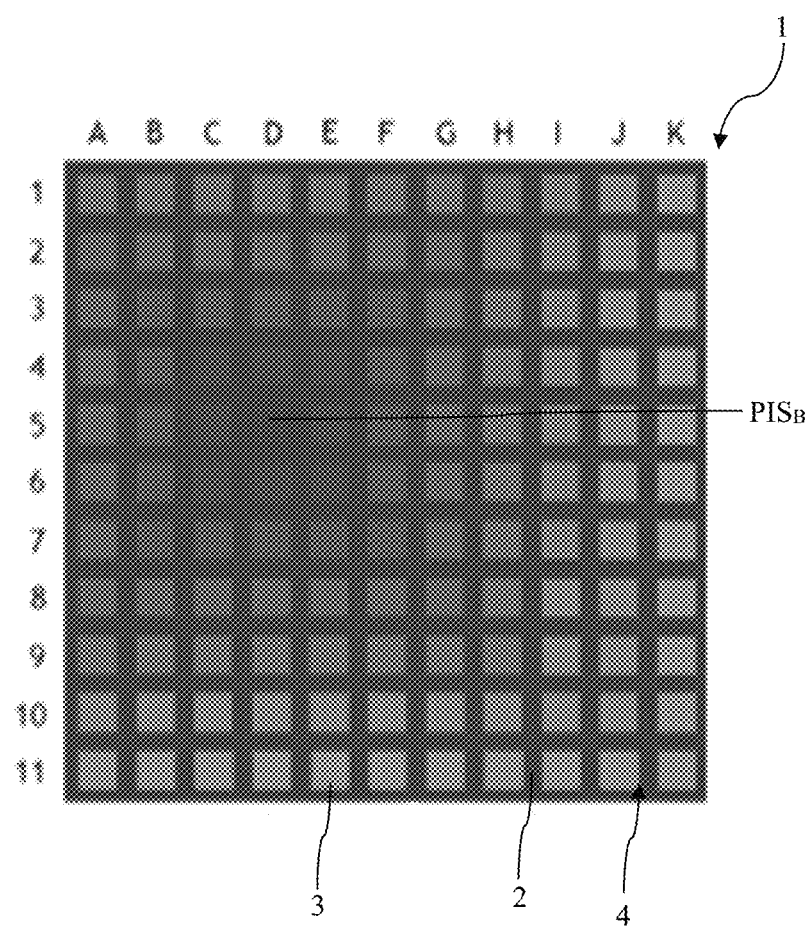

The test carrier 1 of FIG. 8C comprises example color B (light brown). The background 2 comprises a reflectance curve shape rf1 different from the reflectance curve shape rf2 of the samples 3 (as can be seen from FIG. 10). The pseudo-isochromatic spot $PIS_B$ is at position D5.

Figure 8D:
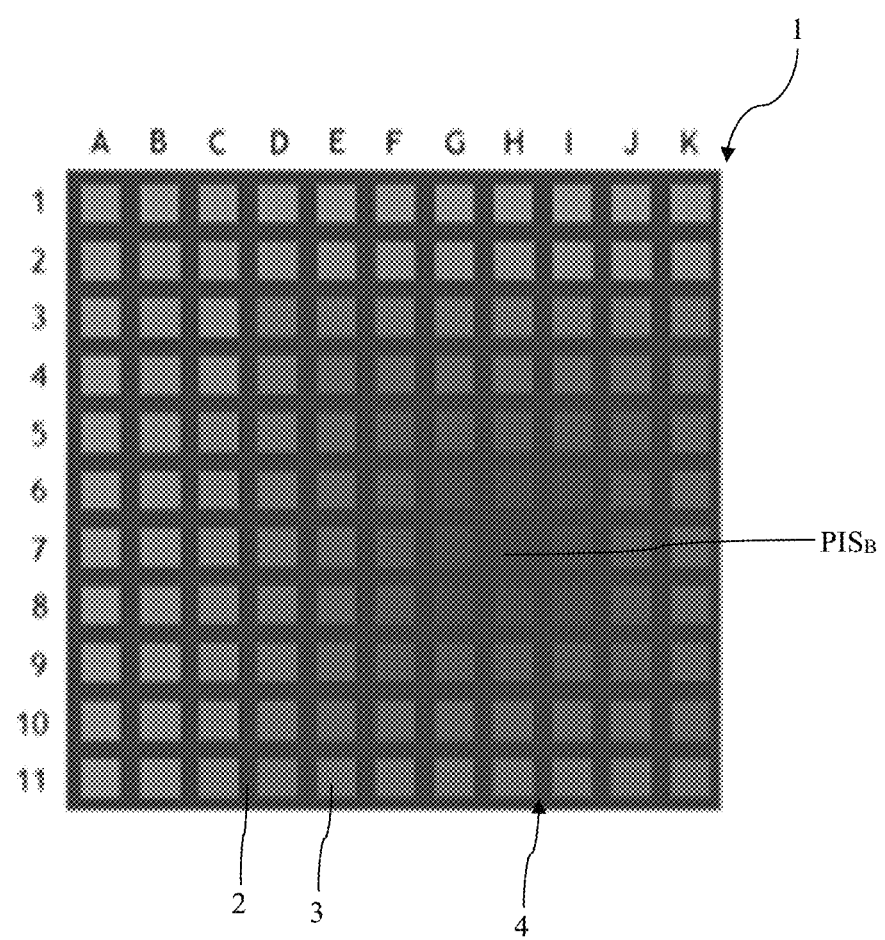

The test carrier 1 of FIG. 8D also comprises example color B (light brown). The background 2 comprises a reflectance curve shape rf2 different from the reflectance curve shape rf3 of the samples 3 (as can be seen from FIG. 10). The pseudo-isochromatic spot $PIS_B$ is at position H7.

Figure 9:
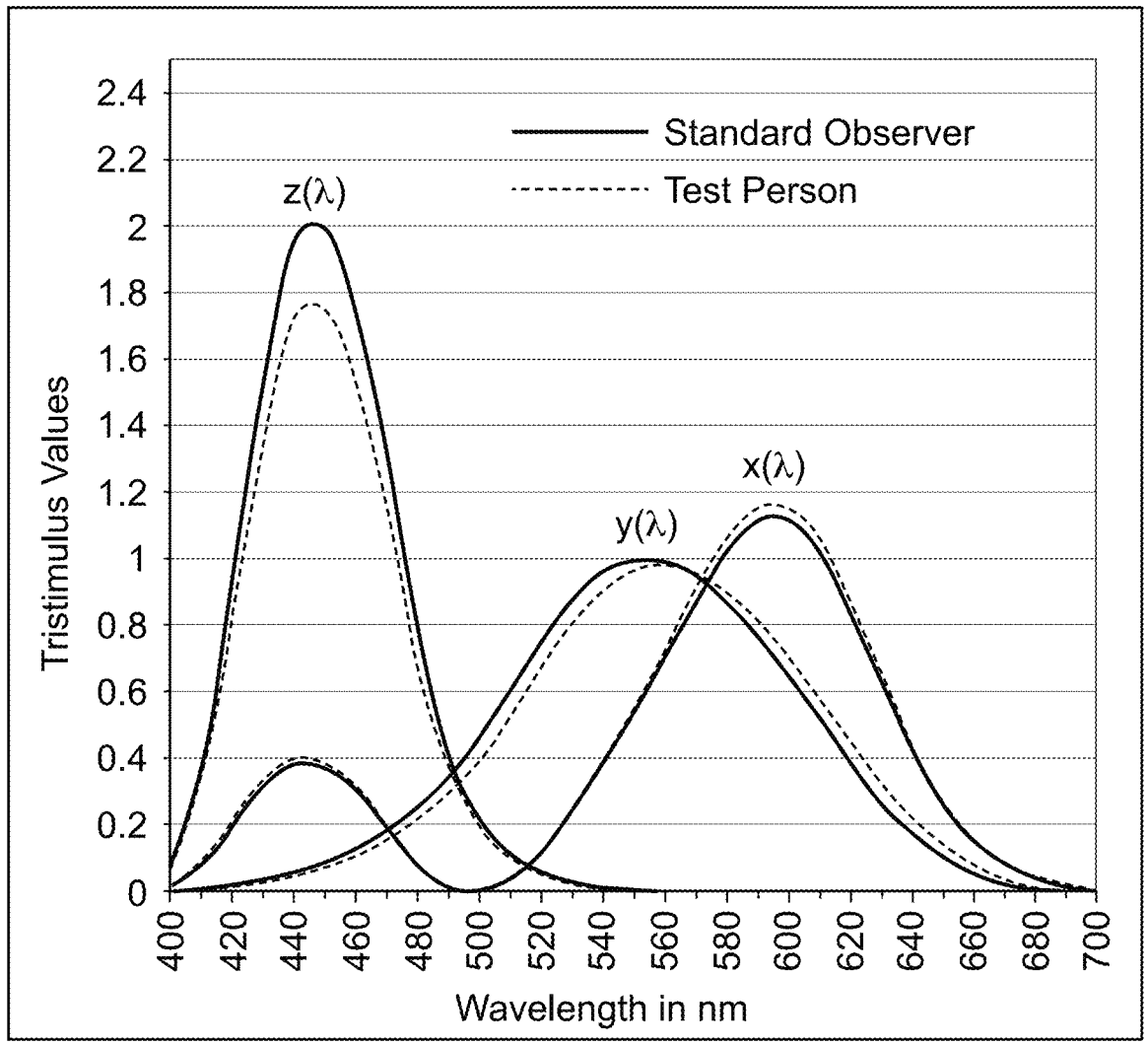
FIG. 9 shows a graph illustrating the predicted color matching functions (CMFs) of the test person versus a standard observer.

FIG. 9 illustrates the determined/predicted color matching functions x ($\lambda$)=X, y ($\lambda$)=Y and z ($\lambda$)=Z of the test person (see dashed line) based on all pseudo-isochromatic spots $PIS_C$ selected during an exemplary test cycle. The generic algorithm predicts the color matching functions based on a particular standard observer (see solid line) and based on the particular spectral power distribution (SPD) of the test illuminant unit 5.

It is noted that the human eye with normal vision has three kinds of cone cells that sense light, having peaks of spectral sensitivity in short ("S", 420 nm-440 nm), middle ("M", 530 nm-540 nm), and long ("L", 560 nm-580 nm) wavelengths. These cone cells underlie human color perception in conditions of medium and high brightness; in very dim light color vision diminishes, and the low-brightness, monochromatic "night vision" receptors, denominated "rod cells", become effective. Thus, three parameters corresponding to levels of stimulus of the three kinds of cone cells, in principle describe any human color sensation. Weighting a total light power spectrum by the individual spectral sensitivities of the three kinds of cone cells renders three effective values of stimulus; these three values compose a tristimulus specification of the objective color of the light spectrum ("tristimulus values").

Figure 10:
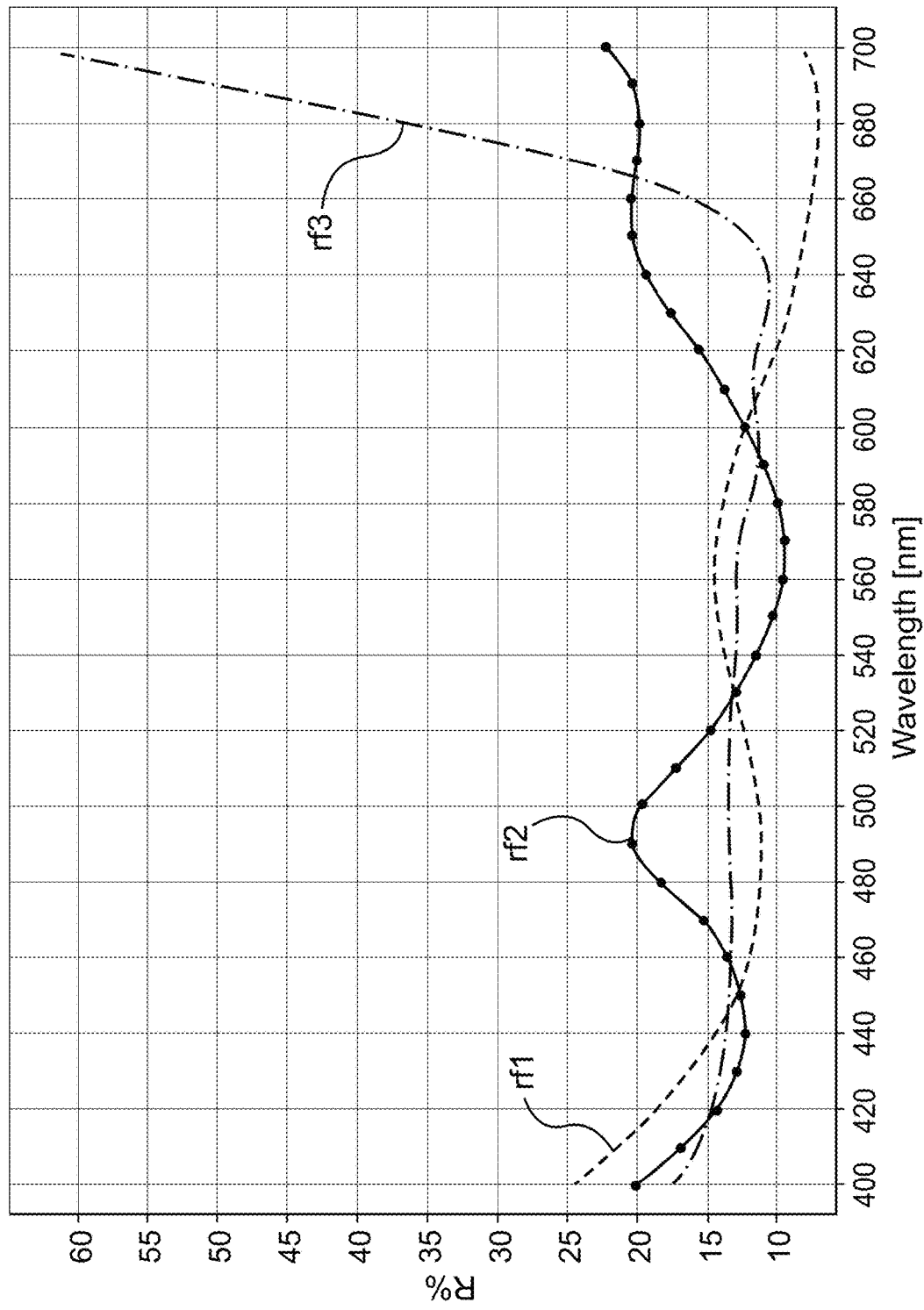
FIG. 10 shows a graph with three curves representing examples for spectral reflectance curve shapes 1, 2 and 3 of FIGS. 8A-8D.

Background 2 and sample 3 at the pseudo-isochromatic spot are colored by different dyestuff combinations showing distinctly different spectral reflectance curve shapes still showing the same color when computed with a particular standard observer (such as CIE standard observer 1964-10°) and a standard daylight illuminant (such as CIE D65). The three curves of FIG. 10 represent examples for spectral reflectance curve shapes rf1, rf2 and rf3 as described above in relation with FIG. 8.

Figure 11:
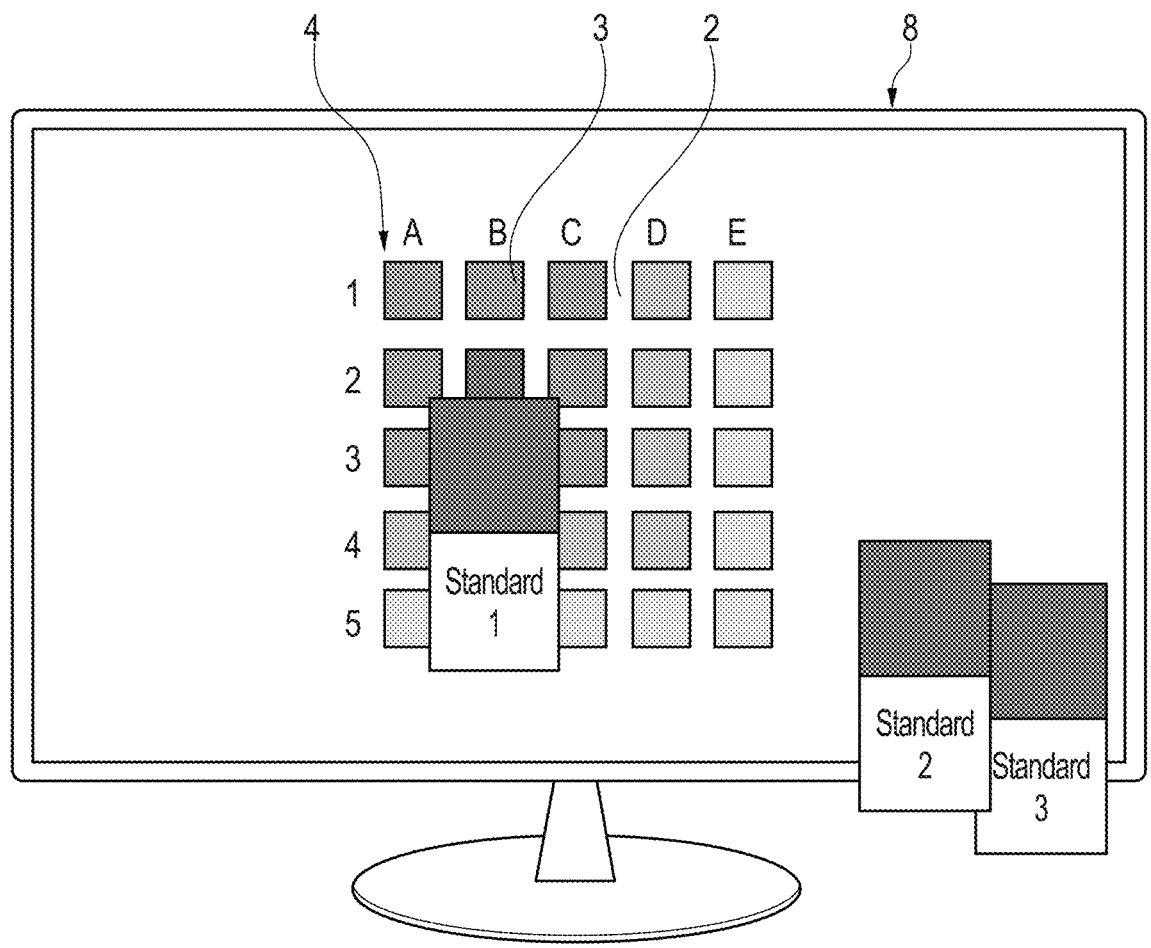
FIG. 11 shows an alternative test system according to the invention where scaling samples are presented on a calibrated screen.

FIG. 11 depicts an alternative test arrangement where scaling samples 3 are presented on a calibrated screen and only the color standard is available in a physical format (printed, coated or otherwise colored). More than one color standard can be used for the same set of scaling samples 3 where color standards are varying in their color constancy (i.e., different spectral reflectance curve shapes). In other words, here the color standard equals the background of the previous examples. The term "background" thus also includes the color standards of this embodiment.

Figure 12:
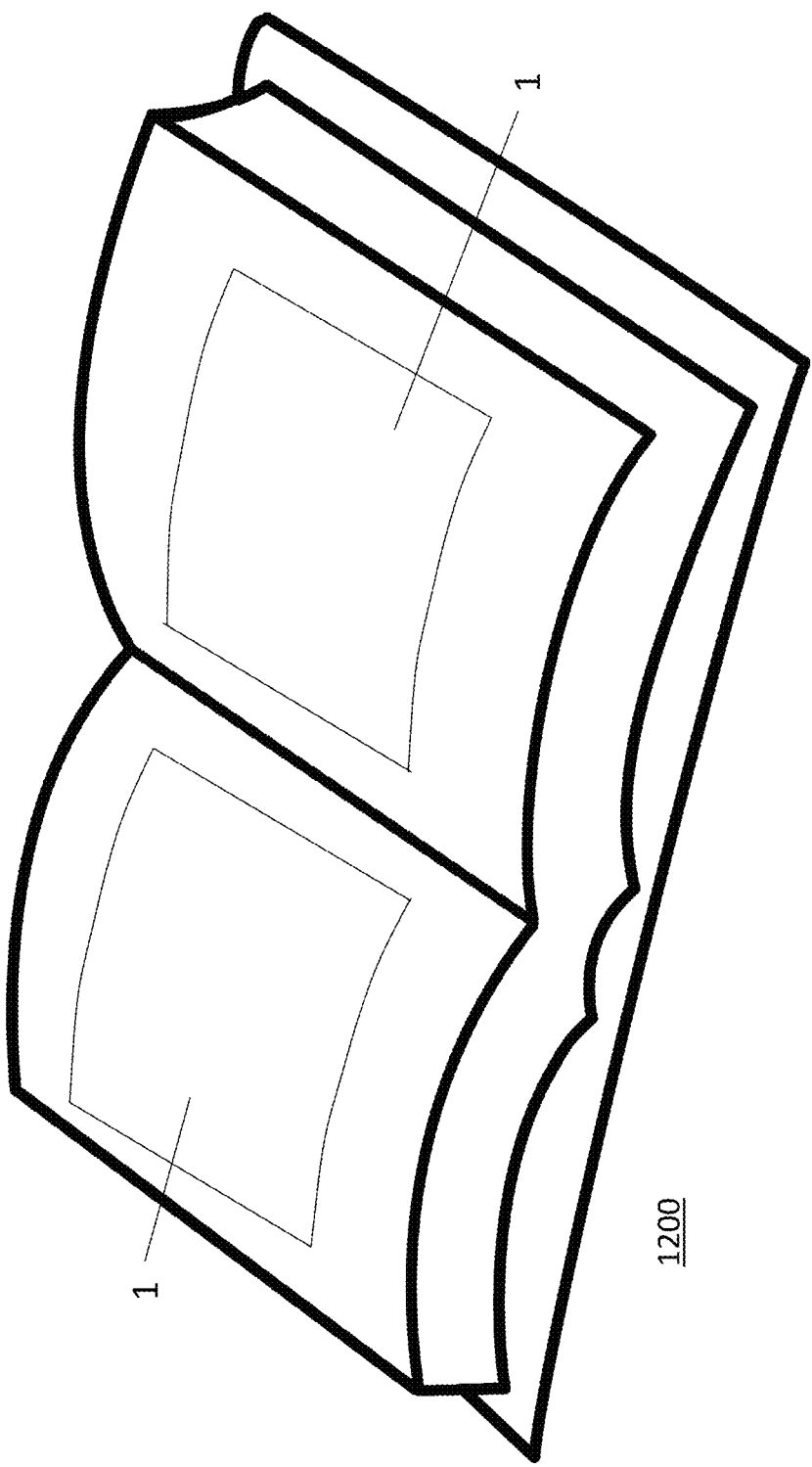
FIG. 12 shows at least two test carriers in a book-like form.

FIG. 12 shows at least two test carriers 1 in a book-like form 1200.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the figures individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage.

The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

LIST OF REFERENCE NUMBERS 1 test carrier
2 background
3 sample
4 two-dimensional pattern
5 test illuminant unit
6 processing unit
7 test person
8 calibrated screen
9 measuring device (SPD)
rf1-3 reflectance curves
$PIS_A$ pseudo-isochromatic spot for standard observer and standard illuminant
$PIS_B$ pseudo-isochromatic spot computed for standard observer and test illuminant
$PIS_C$ pseudo-isochromatic spot selected by test person at test illuminant conditions

What is claimed is:

1. A test system for assessing color vision variability of test persons, the test system comprising:
at least two test carriers, wherein each of the at least two test carriers is provided with a two-dimensional pattern including a background and a plurality of samples,
wherein the plurality of samples and the background of each one of the at least two test carriers are colored with at least two different dyestuff combinations representing metameric colors,
wherein the plurality of samples are arranged in a two-dimensional pattern and the background separates each of the plurality of samples, and
wherein the plurality of samples and/or the background show color scaling in at least two directions such that each one of the at least two test carriers is configured to provide that a test person can select a pseudoisochromatic spot from the two-dimensional pattern where the metameric colors of the plurality of samples and the background match best according to the test person;
a test illuminant unit configured to provide light for color vision variability assessment, the light having a specific spectral power distribution; and
a processing unit configured to determine a congenital and/or acquired color vision deficiency of the test person by calculating a variation of the pseudoisochromatic spot selected by the test person as compared to a reference spot computed by the processing unit based on data of a predefined standard observer considering the specific spectral power distribution of the light of the test illuminant unit.

2. The test system according to claim 1, wherein the at least two test carriers comprise a test carrier with color scaling in smaller steps and a test carrier with color scaling in larger steps.

3. The test system according to claim 1, wherein the plurality of samples of at least one test carrier are configured such that their color scaling is in-line with their spatial distance.

4. The test system according to claim 1, wherein each of the two-dimensional patterns of the at least two test carriers comprises a grid structure.

5. The test system according to claim 1, wherein the plurality of samples and/or the background show color scaling in four directions.

6. The test system according to claim 5, wherein the four directions include 0° for yellower color scaling, 90° for redder color scaling, 180° for bluer color scaling and 270° for greener color scaling.

7. The test system according to claim 1, wherein the at least two test carriers are in book-like form and having different colors and patterns.

8. The test system according to claim 1, wherein the at least two test carriers include patterns of different size.

9. The test system according to claim 1, further comprising a spectrophotometer configured to measure a spectral power distribution of the test illuminant unit.

10. The test system according to claim 1, wherein the test illuminant unit comprises a light cabinet that simulates daylight.

11. The test system according to claim 1, wherein the data of the predefined standard observer represents a CIE standard observer.

12. The test system according to claim 11, wherein the CIE standard observer is a CIE-1964-10° standard observer at CIE-D65 standard daylight.

13. The test system according to claim 11, wherein the CIE standard observer is a CIE-1931-2° standard observer at CIE-D65 standard daylight.

14. The test system according to claim 1, wherein the at least two test carriers include special test carriers configured to provide no pseudoisochromatic spots for a CIE standard observer but by test persons having a congenital or acquired color vision deficiency.

15. The test system according to claim 1, wherein the processing unit forms a color vision variability index based on variations of pseudoisochromatic spots selected by the test person as compared to pseudoisochromatic spots computed based on the data of the predefined standard observer.

16. A test system for assessing color vision variability of test persons, the test system comprising:
a calibrated display screen having at least two test carriers displayed thereon, wherein each of the at least two test carriers is provided with a two-dimensional pattern including a background and a plurality of samples,
wherein the plurality of samples are arranged in a two-dimensional pattern and the background separates each of the plurality of samples, and
wherein the plurality of samples and/or the background show color scaling in at least two directions such that each one of the at least two test carriers is configured to provide that a test person can select a pseudoisochromatic spot from the two-dimensional pattern where metameric colors of the samples and the background match best according to the test person;
a test illuminant unit configured to provide light for assessing the color vision variability, the light having a specific spectral power distribution; and
a processing unit configured to determine a congenital and/or acquired color vision deficiency of the test person by calculating a variation of the pseudoisochromatic spot selected by the test person as compared to a reference spot computed by the processing unit based on data of a predefined standard observer considering the specific spectral power distribution of the light of the test illuminant unit.

* * * * *